US008159236B2

(12) United States Patent
Klenker

(10) Patent No.: US 8,159,236 B2
(45) Date of Patent: Apr. 17, 2012

(54) CORONA EFFLUENT SENSING DEVICE

(75) Inventor: Richard Klenker, Oakville (CA)

(73) Assignee: Xerox Corporation, Norwalk, CT (US)

( * ) Notice: Subject to any disclaimer, the term of this patent is extended or adjusted under 35 U.S.C. 154(b) by 384 days.

(21) Appl. No.: 12/418,488

(22) Filed: Apr. 3, 2009

(65) Prior Publication Data
US 2010/0253360 A1     Oct. 7, 2010

(51) Int. Cl.
*G01R 27/08* (2006.01)
(52) U.S. Cl. .................. 324/691; 324/455; 324/464
(58) Field of Classification Search .......... 324/525, 324/455
See application file for complete search history.

(56) References Cited

U.S. PATENT DOCUMENTS

| 3,908,164 | A  * | 9/1975 | Parker ........................... 323/265 |
| 4,086,650 | A    | 4/1978 | Davis et al. |
| 5,781,003 | A  * | 7/1998 | Kondo ............................ 324/96 |
| 7,030,633 | B1 * | 4/2006 | Qiu et al. ..................... 324/719 |
| 7,209,613 | B2 * | 4/2007 | Liang et al. ................... 385/100 |
| 7,548,066 | B2 * | 6/2009 | Ichimura et al. .............. 324/458 |
| 7,667,179 | B2 * | 2/2010 | Ogawa et al. .............. 250/208.1 |
| 7,732,116 | B2 * | 6/2010 | Weiss et al. ................ 430/108.5 |

FOREIGN PATENT DOCUMENTS
WO    WO 2007/138506 A1    12/2007

OTHER PUBLICATIONS

Journal of Imaging Science, The Effect of Electrode Materials on $O_3$ and $NO_x$ Emissions by Corona Discharging, vol. 32, No. 5, Sep./Oct. 1988, pp. 205-210.
Applied Optics Supplement, "Nature of Charge Carriers in Negative Coronas," 3, 1969, pp. 106-110.
EP Application Serial No. 10158969.5, Search Report dated Jun. 30, 2010, 3 pages.
Nuclear Instruments and Methods in Physics Research A 512 (2003), *"Detectors based on organic materials: status and perspectives,"* D. Natali and M. Sampierto, pp. 419-426.

* cited by examiner

*Primary Examiner* — Richard Isla Rodas
(74) *Attorney, Agent, or Firm* — Pillsbury Winthrop Shaw Pittman LLP

(57) ABSTRACT

The presently disclosed embodiments are directed to the detection and monitoring of corona effluent. The present embodiments pertain to a corona sensing device that employs a film of organic charge transporting material, as the active component in a corona effluent sensing device, that is disposed onto a patterned electrode bearing support member.

15 Claims, 3 Drawing Sheets

CORONA EFFLUENT SENSING DEVICE

BACKGROUND

The present invention relates to a corona effluent sensor using patterned metallic electrodes and a film containing an organic charge transporting molecule in a polymer matrix as a corona sensing element.

Conventionally, corona sensors have been based on the measurement of the ultraviolet, infrared, or ultrasonic emissions associated with corona generation, or on the electrical interaction of the corona ions with a metallic electrode. Corona sensors of these types have been employed in various settings to monitor corona emission due to its damaging effect on electrical components such as transformers, capacitors, electric motors, and generators. Corona effluents progressively damage the insulation inside these devices leading to equipment failure and potentially hazardous electrical arching. Additionally, corona effluents can be hazardous to human health.

Existing methods for sensing corona that are based on the measurement of the ultraviolet, infrared, or ultrasonic emissions, or on the electrical interaction with a metallic electrode require constant electrical power when measuring and can be prohibitively expensive or impractical to implement in all desired settings.

SUMMARY

According to aspects illustrated herein, there is provided a corona sensing device, comprising: a support member, a first electrode and a second electrode placed on the support member, a semiconducting film disposed on the support member and the first and second electrodes, the semiconducting film comprising an organic charge transporting material, and a first wire lead and a second wire lead allowing for connection of the first electrode and the second electrode to an external monitoring circuit.

Another embodiment provides a corona sensing device, comprising: a support member, a first electrode and a second electrode placed on the support member, a semiconducting film disposed on the support member and the first and second electrodes, the semiconducting film comprising an organic charge transporting material comprising from about 20% to about 80% N,N'-diphenyl-N,N'-bis(3-methylphenyl)-1,1'-biphenyl-4,4'-diamine and from about 20% to about 80% polycarbonate, and a first wire lead and a second wire lead allowing for connection of the first electrode and the second electrode to an external resistivity monitoring circuit, wherein a measurement of a decrease in resistivity indicates the detection of corona effluents.

Yet another embodiment provides a method for detecting and monitoring corona effluents, comprising: providing a corona sensing device including a support member, a first electrode and a second electrode placed on the support member, a semiconducting film disposed on the support member and the first and second electrodes, the semiconducting film comprising an organic charge transporting material, and a first wire lead and a second wire lead allowing for connection of the first electrode and the second electrode to an external monitoring circuit, and monitoring for any decrease in resistivity through the semiconducting film with the external circuit, wherein a measurement of a decrease in resistivity indicates the detection of corona effluents.

BRIEF DESCRIPTION OF THE DRAWINGS

For a better understanding, reference may be made to the accompanying figures.

DETAILED DESCRIPTION

Figure 1:
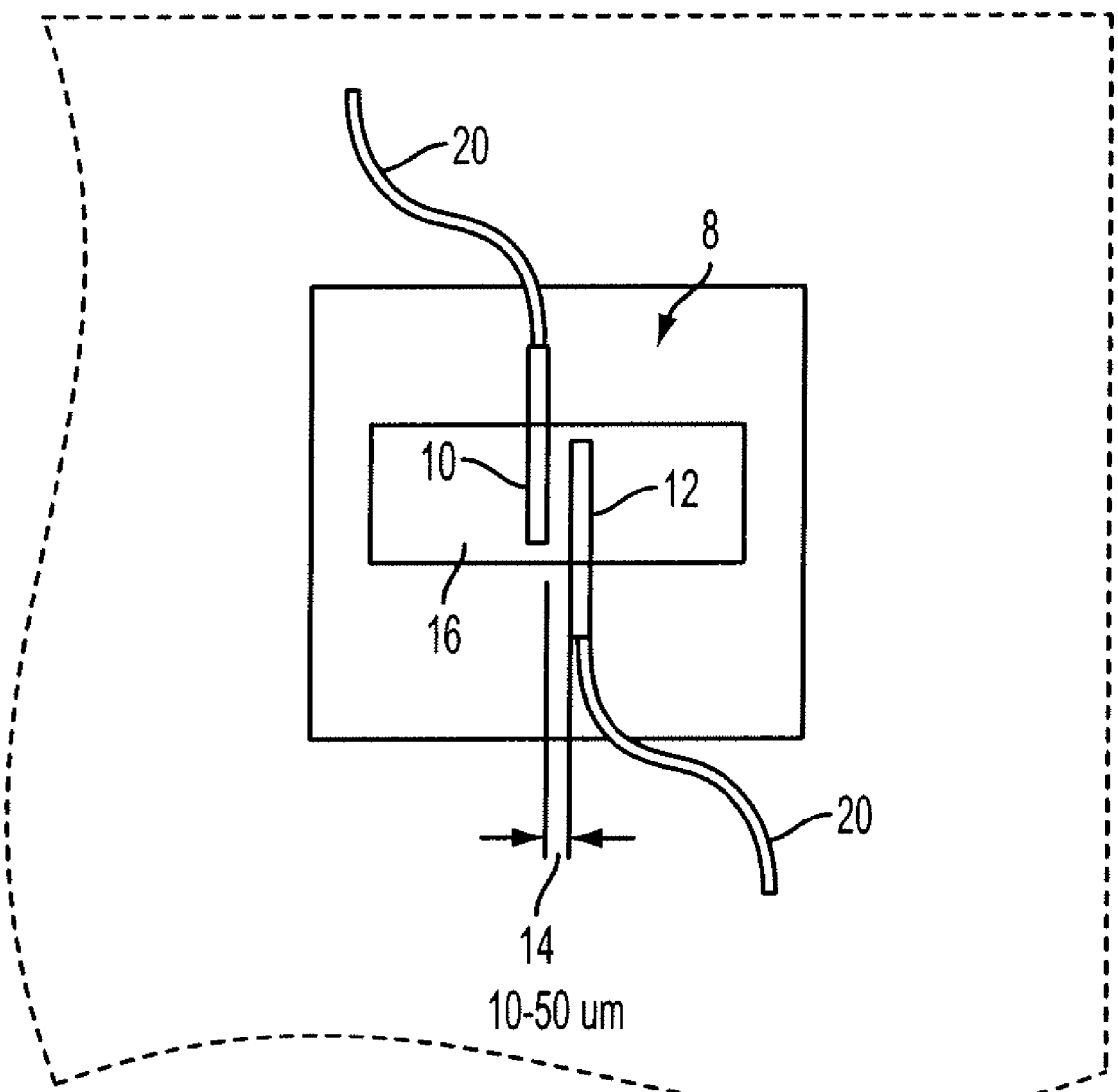
FIG. 1 is a top view of a corona effluent sensing device according to the present embodiments.

In the following description, reference is made to the accompanying drawings, which form a part hereof and which illustrate several embodiments. It is understood that other embodiments may be used and structural and operational changes may be made without departure from the scope of the present disclosure.

The present invention has been made to overcome the above disadvantages of a conventional corona effluent sensor.

An object of the present invention is to provide a corona effluent sensor which is small in size, easy and simple in manufacturing and measurement, and inexpensive.

Another object of the present invention is to provide a corona effluent sensor that has an inherent memory of exposure to corona effluent that has been sensed while the sensor is not connected to any external, power or measurement, circuit.

According to aspects illustrated herein, there is provided a corona effluent sensor comprising: a support member onto which metal electrodes are placed followed by a semiconducting film containing an organic charge transporting molecule in a polymer matrix as a corona sensing element, where the corona sensing element responds to an electric field applied through the electrodes from an external monitoring circuit by transporting electric charge between the electrodes, and where the resistance of the corona sensing element varies reversibly with exposure to corona effluents.

The present embodiments pertain to the use of a film of organic charge transporting material, such as a blend of N,N'-diphenyl-N,N'-bis(3-methylphenyl)-1,1'-biphenyl-4,4'-diamine (TPD) and polycarbonate (PC), as the active component in a corona effluent sensing device. The device comprises a support member onto which two metal electrodes are placed followed by a film of organic charge transporting material. Corona effluent is detected by measuring the decrease in resistivity through the film of organic charge transporting material. The decrease in resistivity is caused by exposure to corona effluents (e.g. $CO_3^-$, $O_3^-$, $NO_2^-$, $O^-$ (Shahin, M. M., Applied Optics Supplement, 3, 106-110, 1969) and $O_3$ and $NO_x$ (Nashimoto, K., Journal of Imaging Science, 32(5), 205-210, 1988)) emitted from a negatively charged corona generating source. This reduction in the resistivity of the organic charge transporting material can be readily detected by a monitoring circuit connected to the device electrodes to indicate the presence of corona effluents. Furthermore, the effect caused by the corona effluents can be reversed by mildly heat treating the sensor or allowing it to rest for a about a week at room temperature so that the corona sensing device can be reset.

Electrical characterization measurements were performed to demonstrate how corona effluents affect the electrical properties of charge transporting films comprised of a blend of 50% TPD and 50% PC. Resistivity measurements of charge transporting films were compared before and after exposure to corona. It was found that exposure to corona effluents generated by a negatively charged corona emitting source reduced the resistivity through the bulk of the charge transporting film. It was further found that the effect that the corona effluent has on the film is measurable for up to a week where the decrease in the effect decayed at an exponential rate. Additionally, it was discovered that the effect of the corona could quickly be removed with a mild heat treatment between 50° C. and 100° C. For a heat treatment at 50° C. it was found that the effect of the corona could be removed in about 30 minutes. The duration required for full recovery from the effect of exposure to corona decreased with increasing heat treatment temperatures within the temperature range of 50° C. to 100° C. Based on these findings, a TPD/PC-based charge transporting film can act as a corona sensor. Thus, the present embodiments describe how an organic semiconducting material may be used as the active material in a negative corona sensing device.

According to the present embodiments, the active component of the device may be comprised of any organic semiconducting material in which the bulk resistivity is sensitive to corona exposure (as described above). As an example, the device (FIG. 1) may comprise a support member 8 onto which metallic charge injecting anode and cathode electrodes 10, 12 are deposited followed by a charge transporting film 16 of TPD blended with PC. As shown in FIG. 1 (top view), these components of the corona sensing device 18 are arranged in a particular configuration so as to allow for charge flow from one electrode 10 to the other electrode 12 through the charge transporting film 16 when the electrodes 10, 12 are appropriately biased. At least a portion of the channel 14 in which the charge flows through the charge transporting film 16 must be exposed to air for sensing purposes. In embodiments, the channel 14 has a width of from about 10 µm to about 50 µm.

In this configuration, an external electronic circuit (not shown) can be connected to the electrodes 10, 12 of the device 18 with, for example, wire leads 20. A constant voltage can be applied by the external circuit such that an electric field is established in the semiconducting film between the electrodes 10, 12. In response to the application of the electric field, charge is transported at a constant flow from one electrode 10 through the semiconducting film 16 to the other electrode 12. This process occurs until the semiconducting film 16 is exposed to corona effluent. At this point, the flow of charge increases as a result of the decrease in resistivity of the semiconducting film 16 due to its interaction with the corona effluent. The difference in the flow of charge through the device 18 while a constant voltage is applied to the electrodes 10, 12, dependent on exposure to the negative corona effluents, may be monitored by the external circuit via the use of an ammeter to measure current or an ohmmeter to measure resistance. In this manner, corona effluents may be detected and monitored while current is constantly flowing through the device 18.

Alternately, the connection of the electrodes 10, 12 of the device 18 to an external electronic circuit (not shown) may be made detachable. Measurements of charge flow through the device 18 may be made before and after it is detached from the monitoring circuit. With this method it may be determined whether or not the device 18 had been exposed to corona effluents while detached from any external circuit by comparing the current or resistance before and after the device 18 may have been exposed.

After exposure to corona, the device 18 can be reset to the pre-exposed state by either allowing it to rest at room temperature for approximately one week or by heat treating it above 50° C.

Figure 2:
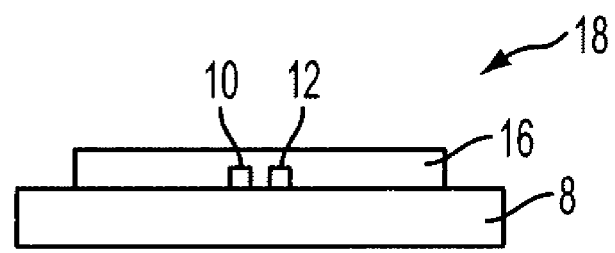
FIG. 2 is a front view of a corona effluent sensing device according to the present embodiments.
Figure 3:
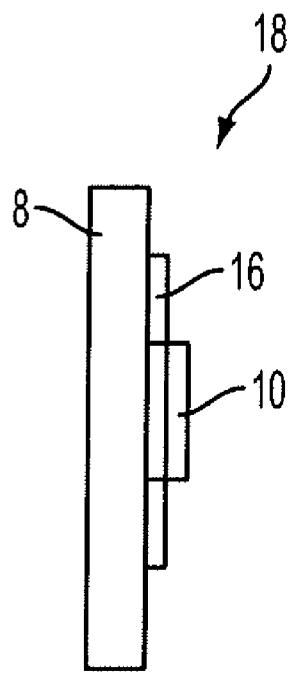
FIG. 3 is a side view of a corona effluent sensing device according to the present embodiments.

FIG. 2 and FIG. 3 show alternative views of the corona sensing device. Namely, FIG. 2 illustrates a front view of the corona sensing device and FIG. 3 illustrates a side view of the corona sensing device.

With this particular arrangement, the sensing device 18 may be fabricated by applying the electrodes 10, 12 by physical vapor deposition (vacuum deposition) through an appropriately patterned shadow mask on to the support member 8, such as for example, a MYLAR film available from DuPont. The film of TPD (50%)/PC (50%) charge transporting material 16 could be coated from a solution with dichloromethane onto the support member 8 overtop of the electrodes 10, 12 in such a way as to leave a portion of each electrode uncoated (as shown in FIG. 1) so that a connection may be made from the electrodes to an external circuit (not shown). The thickness of the TPD/PC film would in part define the sensitivity of the device 18. A suitable thickness would be from about 0.2 µm to about 20 µm. The separation distance between the electrodes will in part define the requirements for the external monitoring circuitry. A suitable separation distance may be from about 10 µm to about 50 µm. The electrode material may be any metallic material that allows for hole and electron injection into the semiconducting film. For example, the electrode material may be selected from the group consisting of platinum, palladium, gold, silver, aluminum, and the like, or any combination thereof.

In the corona sensing device of FIG. 1, FIG. 2, and FIG. 3, the semiconducting film changes upon exposure to corona and the change is measured with the external monitoring circuit. Because resistivity of the semiconducting film decreases with exposure, the external monitoring circuit may be an ohmmeter to measure the change in resistivity. In alternative embodiments, because the change in resistivity manifests itself as an increase in charge flow after exposure, the external monitoring circuit may also be an ammeter used to measure change in current flow. In yet further embodiments, the external monitoring circuit may be any type of circuit—such as an ohmmeter, ammeter, and the like—capable of measuring changes in the semiconducting film upon exposure to corona.

FIG. 2 and FIG. 3 show alternative views of the corona sensing device. Namely, FIG. 2 illustrates a front view of the corona sensing device and FIG. 3 illustrates a side view of the corona sensing device.

Physical vapor deposition may alternately be used if it is not possible to solution coat the active material. As well, sputtering, e-beam evaporation, lithography, etc., could be used to dispose the electrodes.

While the description above refers to particular embodiments, it will be understood that many modifications may be made without departing from the spirit thereof. The accompanying claims are intended to cover such modifications as would fall within the true scope and spirit of embodiments herein.

The presently disclosed embodiments are, therefore, to be considered in all respects as illustrative and not restrictive, the scope of embodiments being indicated by the appended claims rather than the foregoing description. All changes that come within the meaning of and range of equivalency of the claims are intended to be embraced therein.

EXAMPLES

The examples set forth herein below are illustrative of the capability of the proposed sensing devices to measure corona effluents under different conditions that can be used in practicing the present embodiments. It will be apparent, however, that the present embodiments can be practiced with many types of compositions and can have many different uses in accordance with the disclosure above and as pointed out hereinafter.

Example 1

A corona effluent sensing device was assembled in the following manner. Gold electrodes were patterned, as depicted in FIG. 1, onto a MYLAR (DuPont) substrate by physical vapor deposition and the use of a shadow mask. TPD charge transport molecule and bisphenol A polycarbonate were put into a dichloromethane solution at the weight ratio of 1:1. A solution wherein the dissolved solids content of 17% was prepared. By using this solution a film of about 12 µm thickness was blade coated onto the gold electrode bearing MYLAR (DuPont) substrate in such a way as to leave a portion of each electrode uncoated, as depicted in FIG. 1. A wire lead was then attached to the uncoated portion of each electrode with electrically conductive glue. The device was left to dry in air at room temperature for 12 hours, was then heated in air to 120° C. for 0.5 hours, and then allowed to cool in air at room temperature for 1 hour.

A corona source of the type described in U.S. Pat. No. 4,086,650 to Davis et al., commonly referred to in the art as a scorotron was used as a stable, tunable, and positionable negative corona effluent emitter. The scorotron is comprised of a corona wire with a conductive control grid or screen of parallel wires in a plate positioned between the corona wire and the corona sensing device. To generate negative corona the scorotron is operated by applying a constant current to the corona wire in the order of hundreds of microamperes giving an applied potential in the order of kilovolts. A potential is applied to the control grid of the same polarity as the corona potential but with a much lower voltage, usually several hundred volts, which suppresses the electric field between the surface to be charged and the corona wire and can markedly reduce the emitted ion current flow. Increasing or decreasing the control grid voltage allows for respectively greater and lesser ion current flow from the scorotron.

An ammeter and a constant voltage power supply were used as the external monitoring circuit. The ammeter and power supply were connected to the wire leads of the sensing device such that an electric field could be established in the semiconducting film and current flow could be measured between the electrodes.

Figure 4:
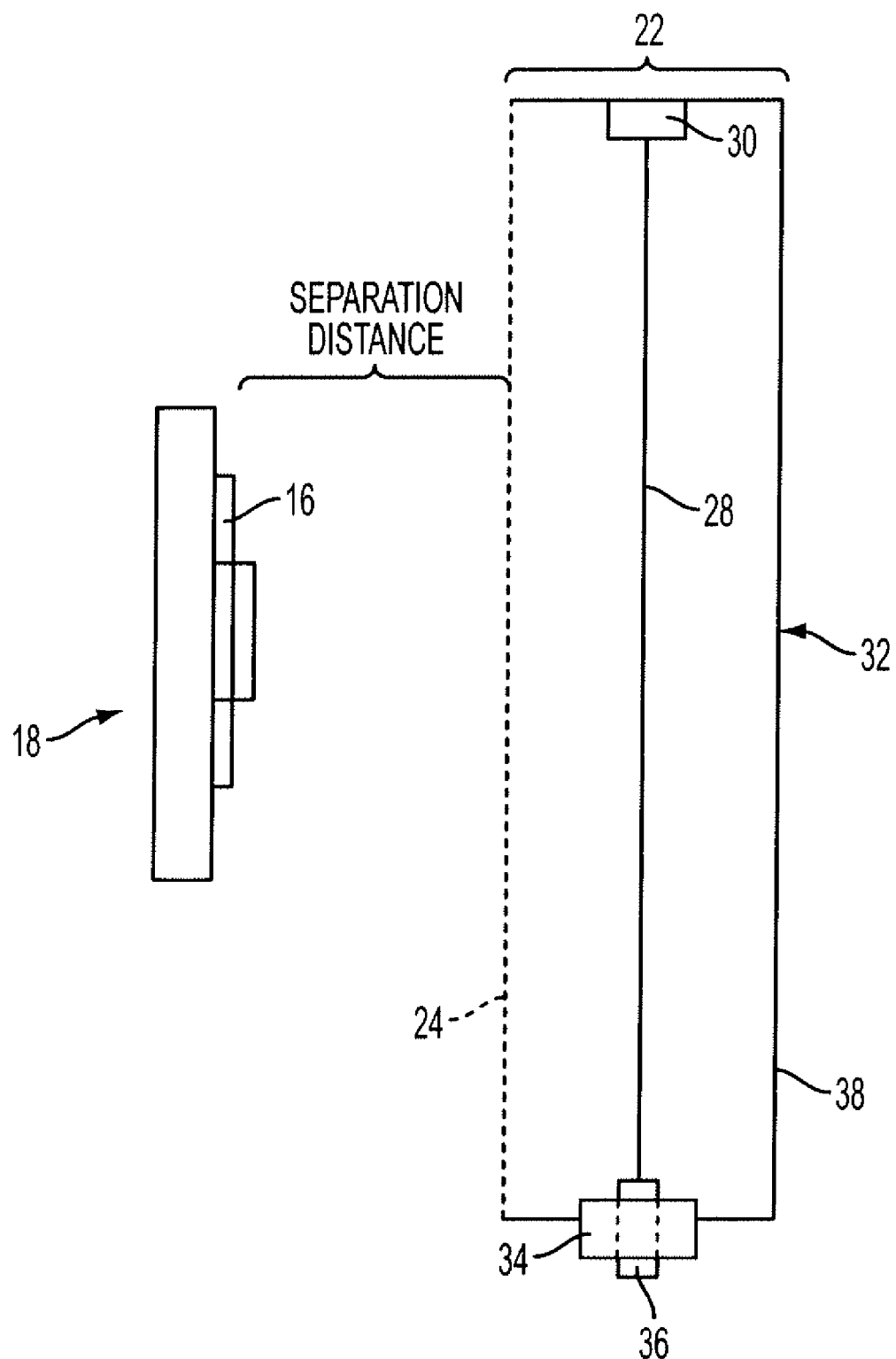
FIG. 4 is a view schematically showing an arrangement of a corona effluent sensing device according to the present embodiments and a corona source of the type commonly referred to in the art as a scorotron.

As shown in FIG. 4, the scorotron 22 and sensing device 18 were fixed in position so that the control grid 24 and the semiconducting film 16 of the sensing device 18 were facing at separation distance 26. In embodiments, the separation distance 26 may be about 2 cm apart. The scorotron 22 includes a corona wire 28 and an insulating mount 30 for the corona wire 28. A metallic shield 32 envelops the corona wire 28 and is connected to the control grid 24. The scorotron 22 and sensing device 18 were placed into a 30 cm×25 cm×39 cm sized box (not shown) with a lid and a feed-through for the wire leads 36, 38 so that a corona effluent sensor device test fixture was formed. Wire lead 36 connects the corona wire 28 to the constant current power supply (not shown) and wire lead 38 connects the metallic shield 32 and control grid 24 to the constant voltage power supply (not shown).

The test fixture thus assembled was operated. A bias of 100 V was continuously applied across the electrodes throughout the entire procedure. Once the bias was applied, a baseline measurement of current flow between the electrodes was performed over the course of 5 minutes. Next, while still maintaining the 100 V bias across the sensor electrodes, the scorotron was energized for a duration of 30 minutes with a −400 µA constant current supplied to the corona wire and a −500 V constant voltage applied to the control grid. At the end of the 30 minute duration the scorotron was turned off, and again current flow was measured over a period of 5 minutes while maintaining the 100 V bias. This procedure of exposing the sensor to corona for 30 minutes, and then measuring current flow was repeated for two more iterations. The results of these measurements, summarized in Table 1, show that the current flow measured across the electrodes varied in accordance with the duration of corona effluent exposure. Thus, a concentration of corona effluents could be qualitatively measured.

TABLE 1

Summary of measurement results from cumulative exposure experiment.

| Cummulative Exposure Duration (mins) | Average Current (pA) | Resistance (based on Average Current) (TOhm) |
| --- | --- | --- |
| 0 | 24 | 4.2 |
| 30 | 82 | 1.2 |
| 60 | 123 | 0.8 |
| 90 | 165 | 0.6 |

Example 2

Another corona effluent sensor device was manufactured by the method described in example 1. Again, an ammeter and a constant voltage power supply were connected to the sensing device and used as the external monitoring circuit as described in example 1. The device was assembled with the scorotron corona source as described in example 1, except that the scorotron was held in place on a rail allowing for the separation distance between the scorotron and sensor device to be adjusted. As in example 1, the scorotron and sensing device were placed in a box so that a corona effluent sensor device test fixture was formed.

The test fixture thus assembled was operated. The separation distance between the scorotron control grid and the sensor surface was adjusted to 2 cm. A 100 V bias was applied across the sensor electrodes while over the course of 5 minutes a baseline measurement of the current flow between the electrodes was performed. Next, the 100 V bias was turned off, and the device was disconnected from the ammeter and power supply. Then the scorotron was energized for the duration of 20 minutes with a −400 µA constant current supplied to the corona wire and a −500 V constant voltage applied to the control grid. At the end of the 20 minute duration the scorotron was turned off, the sensor was allow to rest for 10 minutes, and then the sensor was reconnected to the ammeter and power supply. Next, a 100 V bias was applied across the electrodes while current flow was measured over a period of 5 minutes. The sensor was then disconnected from the ammeter and power supply, heat treated for 1 hour at 65° C., and then allowed to cool in air at room temperature for 0.5 hours. This procedure of measuring current flow at a 100 V bias before and after exposure to corona and then heat treating to reset the sensor was repeated at separation distances of 4.5 cm and 9.5 cm. The results of these measurements, summarized in Table 2, show that the current flow measured across the electrodes varied in accordance with the proximity of the sensor to the corona source and that the sensor may be reset with a heat treatment. Thus, a concentration of corona effluents could be qualitatively measured and the sensor reset by heating.

TABLE 2

Summary of measurement results from proximity of corona source experiment.

| Distance (cm) | Average Current | | Resistance (Based on Average Current) | |
|---|---|---|---|---|
| | Before Exposure (pA) | After 20 mins. Corona Exposure (pA) | Before Exposure (TOhm) | After 20 mins. Corona Exposure (TOhm) |
| 2.0 | 38 | 120 | 2.6 | 0.8 |
| 4.5 | 46 | 77 | 2.2 | 1.3 |
| 9.5 | 49 | 58 | 2.1 | 1.7 |

All the patents and applications referred to herein are hereby specifically and totally incorporated herein by reference in their entirety in the instant specification.

It will be appreciated that several of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A corona sensing device, comprising:
   a support member;
   a first electrode and a second electrode placed on the support member;
   a semiconducting film disposed on the support member and the first and second electrodes, the semiconducting film comprising an organic charge transporting material comprising from about 20% to about 80% N,N'-diphenyl-N,N'-bis(3-methylphenyl)-1,1'-biphenyl-4,4'-diamine and from about 20% to about 80% polycarbonate;
   a first wire lead and a second wire lead allowing for connection of the first electrode and the second electrode to an external resistivity monitoring circuit, wherein a measurement of a decrease in resistivity indicates the detection of corona effluents; and
   a heating device for resetting the corona sensing device after exposure to corona effluents by applying a mild heat treatment of from about 50° C. to about 100° C.

2. The corona sensing device of claim 1, wherein the semiconducting film has a thickness of from about 0.2 µm to about 10 µm.

3. The corona sensing device of claim 1, wherein the first and second electrodes have a thickness of from about 0.05 µm to about 0.2 µm.

4. The corona sensing device of claim 1, wherein a separation distance between the first electrode and the second electrode is from about 10 µm to about 50 µm.

5. A method for detecting and monitoring corona effluents, comprising:
   providing a corona sensing device including
   a support member;
   a first electrode and a second electrode placed on the support member;
   a semiconducting film disposed on the support member and the first and second electrodes, the semiconducting film comprising an organic charge transporting material; and
   a first wire lead and a second wire lead allowing for connection of the first electrode and the second electrode to an external monitoring circuit;
   monitoring for any decrease in resistivity through the semiconducting film with the external circuit, wherein a measurement of a decrease in resistivity indicates the detection of corona effluents; and
   resetting the corona sensing device after exposure to corona effluents by applying a mild heat treatment of from about 50° C. to about 100° C.

6. The method of claim 5, wherein the semiconducting film comprises from about 20% to about 80% charge transporting molecules.

7. The method of claim 6, wherein the charge transporting molecules are selected from the group comprising of N,N'-diphenyl-N,N'-bis(3-methylphenyl)-1,1'-biphenyl-4,4'-diamine (TPD), 1,1-bis((di-4-tolylamino)phenyl)-cyclohexane (TAPC), N,N-bis(3,4-dimethylphenyl)-4-aminobiphenyl (DMPAB), p-diethylaminobenzaldehyde diphenylhydrazone (DEH) and mixtures thereof.

8. The method of claim 7, wherein the charge transporting molecule is N,N'-diphenyl-N,N'-bis(3-methylphenyl)-1,1'-biphenyl-4,4'-diamine (TPD).

9. The method of claim 5, wherein the semiconducting film comprises from about 20% to about 80% polycarbonate of 4,4'-(propan-2-ylidene)diphenol (bisphenol A) or 4,4'-cyclohexylidenebisphenol (bisphenol Z type).

10. The method of claim 5, wherein the semiconducting film comprises about 50% N,N'-diphenyl-N,N'-bis(3-methylphenyl)-1,1'-biphenyl-4,4'-diamine and about 50% polycarbonate.

11. The method of claim 5, wherein the semiconducting film has a thickness of from about 0.2 µm to about 10 µm.

12. The method of claim 5, wherein the first and second electrodes have a thickness of from about 0.05 µm to about 0.2 µm.

13. The method of claim 5, wherein a separation distance between the first electrode and the second electrode is from about 10 µm to about 50 µm.

14. The method of claim 5, wherein the mild heat treatment is applied for about 30 minutes to about 1 hour.

15. A method for detecting and monitoring corona effluents, comprising:
   providing a corona sensing device including
   a support member;
   a first electrode and a second electrode placed on the support member;
   a semiconducting film disposed on the support member and the first and second electrodes, the semiconducting film comprising an organic charge transporting material; and
   a first wire lead and a second wire lead allowing for connection of the first electrode and the second electrode to an external monitoring circuit; and
   detecting corona effluents with the external monitoring circuit by monitoring resistivity through the semiconducting film, any decrease in resistivity through the semiconductor film indicating the presence of corona effluents.

* * * * *